United States Patent
Mandel et al.

(10) Patent No.: US 7,037,725 B2
(45) Date of Patent: *May 2, 2006

(54) METHOD AND SYSTEM FOR CREATING A MERCURY HALIDE STANDARD FOR USE IN TESTING A MERCURY ANALYZER SYSTEM

(75) Inventors: Stephen B. Mandel, Parsippany, NJ (US); Scott M. Shields, Easton, PA (US)

(73) Assignee: Spectra Gases, Inc., Branchburg, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/943,521

(22) Filed: Sep. 17, 2004

(65) Prior Publication Data

US 2005/0054110 A1    Mar. 10, 2005

Related U.S. Application Data

(63) Continuation of application No. 10/356,832, filed on Feb. 3, 2003, now Pat. No. 6,852,542.

(51) Int. Cl.
*G01N 1/22* (2006.01)
*G01N 33/20* (2006.01)

(52) U.S. Cl. .............. 436/81; 436/8; 436/9; 436/124; 436/181; 422/83

(58) Field of Classification Search ............... 436/81, 436/8, 9, 124, 181, 18, 73, 166, 174; 422/83
See application file for complete search history.

(56) References Cited

U.S. PATENT DOCUMENTS

| | | | |
|---|---|---|---|
| 4,643,215 A * | 2/1987 | Phlipot et al. ........... 137/15.01 |
| 5,679,957 A | 10/1997 | Durham et al. |
| 5,733,786 A | 3/1998 | Green |
| 5,900,042 A | 5/1999 | Mendelsohn et al. |
| 6,136,281 A | 10/2000 | Meischen et al. |
| 6,375,909 B1 | 4/2002 | Dangtran et al. |
| 6,475,802 B1 | 11/2002 | Schaedlich et al. |
| 6,690,462 B1 | 2/2004 | Seltzer |
| 6,808,692 B1 * | 10/2004 | Oehr ........................ 423/210 |
| 2002/0068030 A1 | 6/2002 | Nolan et al. |
| 2003/0161771 A1 | 8/2003 | Oehr |

OTHER PUBLICATIONS

"The PSA Calibration Scheme" (no publication available).
www.gcind.com/calibrators.htm; Aug. 29, 2003; pp. 1-2.
www.gcind.com/chemicals.htm; Aug. 29, 2003; pp. 1-3.
www.gcind.com/permeation.htm; Aug. 29, 2003; pp. 1-2.
www.seefelder-messtechnik.com/U73-5-01-general-e.pdf; pp. 1-4.
www.vici.com/calib/dynacal.htm; Sep. 2, 2003; pp. 1-3.
www.vici.com/calib/perm.htm; Sep. 2, 2003; pp. 1-2.
www.vici.com/calib/permtube.pdf; Sep. 2, 2003; pp. 1-2.

* cited by examiner

*Primary Examiner*—Maureen M. Wallenhorst
(74) *Attorney, Agent, or Firm*—Lerner, David, Littenberg, Krumholz & Mentlik, LLP

(57) ABSTRACT

A method and system are provided for creating a mercury halide standard, and for using that standard to test a mercury analyzer system. Gaseous elemental mercury of a known concentration from a gas cylinder and a halogen donor are fed to a reaction chamber where they react to form mercury halide. The mercury halide is fed to a mercury analyzer system where it is converted to reform gaseous elemental mercury which is then measured by a mercury analyzer. By comparing either the amount of elemental mercury supplied to the reaction chamber or the amount of mercury halide formed in the reaction chamber with the amount of elemental mercury converted from the mercury halide, the ability of the mercury analyzer system to convert mercury halide to gaseous elemental mercury can be evaluated.

7 Claims, 2 Drawing Sheets

METHOD AND SYSTEM FOR CREATING A MERCURY HALIDE STANDARD FOR USE IN TESTING A MERCURY ANALYZER SYSTEM

CROSS-REFERENCE TO RELATED APPLICATIONS

The present application is a continuation of U.S. patent application Ser. No. 10/356,832, filed Feb. 3, 2003, now U.S. Pat. No. 6,852,542 issued on Feb. 8, 2005, the disclosure of which is incorporated by reference herein.

BACKGROUND OF THE INVENTION

The present invention relates to a method and system for creating a mercury halide standard. More particularly, the present invention relates to a method and system for creating a mercury halide standard for use in testing a mercury analyzer system.

Mercury pollution has been determined to have a detrimental effect on humans. It particularly affects women of childbearing age and people who frequently consume contaminated fish. At high doses, mercury exposure can cause tremors, inability to walk, convulsions, or death. The developing human fetus is the most sensitive to the effects of mercury. Exposure to mercury in the developing fetus can cause delayed onset of walking and talking, cerebral palsy, and reduced neurological test scores.

Elemental mercury, $Hg^0$, can have a lifetime in the atmosphere of six to twelve months before being deposited far away from the source of the mercury. Ionic mercury, Hg (II) or $Hg^{+2}$, is water soluble and is another common pollutant that typically forms as mercury chloride, $HgCl_2$. Mercury chloride often results from combustion processes that have free chlorine, such as coal-fired power plants and waste incinerators.

There have been numerous devices designed to measure the amount of mercury present in a specimen such as that described in U.S. Pat. No. 6,475,802 to Schaedlich et al., and titled "Apparatus For and Method of Collecting Gaseous Mercury and Differentiating Between Different Mercury Components." Typical of these devices are systems that include a mercury analyzer. Such analyzers read only elemental mercury. Any $Hg^{+2}$ must first be converted to elemental mercury in the system before being analyzed. If all the $Hg^{+2}$ is converted to elemental mercury, an accurate measurement of the amount of mercury in the specimen can be obtained. However, if any $Hg^{+2}$ is not converted, the analyzer will not read it, and the resulting measurement will not accurately reflect total mercury content. The success of the conversion, therefore, impacts the accuracy of the measurements made by such analyzers.

In view of the foregoing, there is a need to test the completeness of the conversion from $Hg^{+2}$ to elemental mercury within these systems. The test results will enable the analyzers to accurately measure the total elemental mercury and $Hg^{+2}$ content in the specimen.

SUMMARY OF THE INVENTION

The present invention addresses this need.

One aspect of the present invention provides a method of creating a mercury halide standard. The method includes providing gaseous elemental mercury of a known concentration from a gas cylinder; and providing at least one halogen donor which is reactable with the gaseous elemental mercury. The gaseous elemental mercury is then reacted with the halogen donor to form gaseous mercury halide. Preferably, at least a stoichiometric amount of the halogen donor is reacted with the gaseous elemental mercury.

In a preferred embodiment, the halogen donor is a gas, and more preferably chlorine gas such that the reaction between the gaseous elemental mercury and the halogen donor produces mercury halide. The halogen donor may be provided from a gas cylinder.

Another aspect of the present invention is a system for creating a mercury halide standard. This aspect includes a gas cylinder containing gaseous elemental mercury having a known concentration and a source of a halogen donor which is reactable with the gaseous elemental mercury. The source of the gaseous elemental mercury and the source of the halogen donor are in communication with a reaction chamber so that the reaction chamber may receive an amount of both the gaseous elemental mercury and the halogen donor. The gaseous elemental mercury and the halogen donor react in the reaction chamber to form the mercury halide standard.

The system may include a controller between the source of the halogen donor and the reaction chamber for controlling the flow of the halogen donor from the source to the reaction chamber. Preferably, this controller is a plate having an aperture of a predetermined size. The system may further include a controller between the source of gaseous elemental mercury and the reaction chamber for controlling the flow of the gaseous elemental mercury from the gas cylinder to the reaction chamber.

In a preferred embodiment, the halogen donor donates chlorine, preferably in the form of a gas. The gas may be supplied from a gas cylinder.

Yet another aspect of the present invention provides a method of testing a mercury analyzer system having a mercury analyzer. The method includes reacting gaseous elemental mercury with at least a stoichiometric amount of a halogen donor to form a gaseous mercury halide; converting at least a portion of the gaseous mercury halide to reform an amount of gaseous elemental mercury; measuring the amount of reformed gaseous elemental mercury using the mercury analyzer; and comparing the known amount of the gaseous mercury halide with the reformed amount of gaseous elemental mercury to determine a degree of conversion from the gaseous mercury halide to gaseous elemental mercury in the converting step. In a highly preferred embodiment of the invention, the method is performed in an industrial facility.

In a variant of this method a known amount of gaseous elemental mercury is reacted with at least a stoichiometric amount of a halogen donor to form a gaseous mercury halide; at least a portion of the gaseous mercury halide is converted to reform an amount of gaseous elemental mercury; the reformed amount of gaseous elemental mercury is measured; and the known amount of gaseous elemental mercury is compared with the reformed amount of gaseous elemental mercury to determine the degree of conversion from the gaseous mercury halide to the reformed elemental mercury in the converting step.

Still a further aspect of the present invention includes an apparatus for testing a mercury analyzer system, including a source of gaseous elemental mercury; a source of a halogen donor which is reactable with the gaseous elemental mercury; a reaction chamber in communication with the source of gaseous elemental mercury and the source of the halogen donor so as to receive an amount of the gaseous elemental mercury and the halogen donor, the gaseous elemental mercury and the halogen donor reacting in the reaction chamber to form a known amount of gaseous mercury halide; a conversion module for converting at least a portion of the gaseous mercury halide to reform an amount of gaseous elemental mercury; measuring means in the mercury analyzer system for measuring the reformed amount of gaseous elemental mercury; and comparing means for comparing the known amount of the gaseous mercury halide with the reformed amount of gaseous elemental mercury to determine a degree of conversion from the gaseous mercury halide to the gaseous elemental mercury in the conversion module.

An alternative embodiment of the apparatus includes a source of gaseous elemental mercury; a source of a halogen donor which is reactable with the gaseous elemental mercury; a reaction chamber in communication with the source of gaseous elemental mercury and the source of the halogen donor so as to receive a known amount of said gaseous elemental mercury and at least a stoichiometric amount of the halogen donor, the gaseous elemental mercury and the halogen donor reacting in the reaction chamber to form gaseous mercury halide; a conversion module for converting at least a portion of the gaseous mercury halide to reform an amount of gaseous elemental mercury; measuring means in the mercury analyzer system for measuring the reformed amount of gaseous elemental mercury; and comparing means for comparing the known amount of the gaseous elemental mercury with the reformed amount of gaseous elemental mercury to determine the degree of conversion of the gaseous mercury halide to the reformed gaseous elemental mercury in the conversion module.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION

Figure 1:
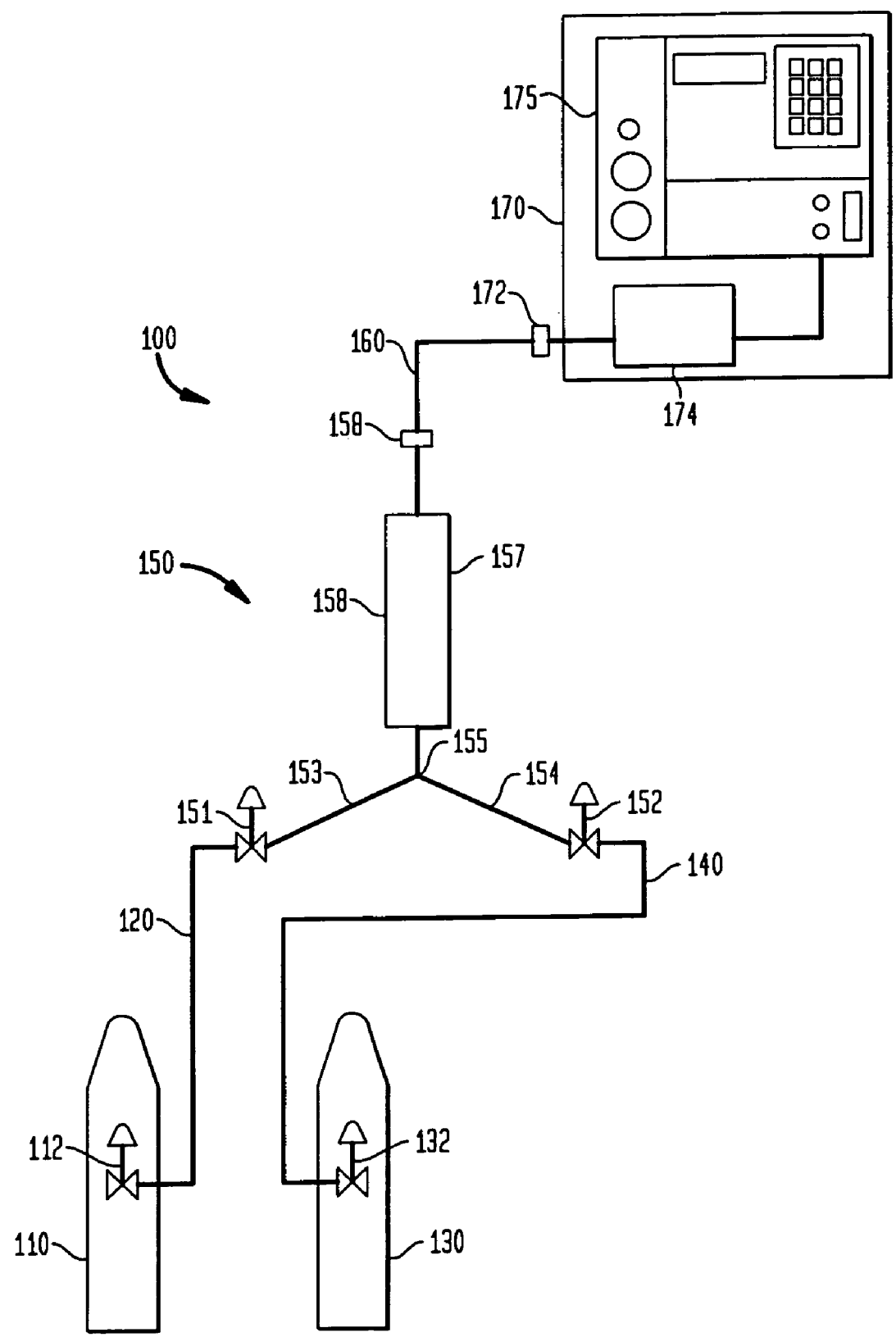
FIG. 1 is a highly schematic diagram of a system for creating a mercury halide standard in accordance with the present invention for use in a mercury analyzer system.

Referring to FIG. 1, a system 100 for creating a mercury halide standard is shown in combination with a well-known mercury analyzer 170. System 100 includes a source of gaseous elemental mercury. While any source of gaseous elemental mercury having a known concentration may be used in the present invention, the gaseous elemental mercury preferably is supplied from a self-contained gas cylinder 110. The source of gaseous elemental mercury generally has a concentration of between about 1 $\mu g/m^3$ and about 100 $\mu g/m^3$, and preferably between about 10 $\mu g/m^3$ and about 50 $\mu g/m^3$. The gaseous elemental mercury may be mixed with an inert carrier gas, such as, for example, nitrogen ($N_2$). One supplier of the desired concentration of gaseous elemental mercury in a gas cylinder is Spectra Gases, Inc. of Branchburg, N.J., USA.

A flexible or rigid conduit 120 connects gas cylinder 110 to one input of a reaction chamber 150, so that the reaction chamber is in communication with cylinder 110. The conduit 120 is preferably made of a material that is inert to the gaseous elemental mercury and the carrier gas. An infinitely adjustable valve 112 controls the flow of mercury gas from cylinder 110 to reaction chamber 150. Ordinarily, valve 112 is on the output of the cylinder 110. However, cylinder 110 may include a simple on/off valve, and infinitely adjustable valve 112 may be positioned anywhere between cylinder 110 and the input of reaction chamber 150.

System 100 also includes a halogen donor. The halogen donor includes any element or compound that will react with elemental mercury to form a mercury halide, for example, chlorine gas, $Cl_2$, or hydrochloric gas, HCl. The halogen donor may be in any form, including a gas, solid, or liquid. A particularly preferred halogen is chlorine, which readily reacts with mercury to form mercury chloride. Preferably, the chlorine is provided from a self-contained gas cylinder 130 containing chlorine gas in a known concentration. The chlorine gas may be mixed with an inert carrier gas, such as, for example, nitrogen ($N_2$) such that, the concentration of the halogen in the gas is known. Cylinders of chlorine gas having known concentrations are commercially available from a variety of suppliers.

A flexible or rigid conduit 140 inert to gaseous chlorine connects chlorine gas cylinder 130 to another input of reaction chamber 150, so that reaction chamber 150 is in communication with cylinder 130. An infinitely adjustable valve 132 controls the flow of chlorine gas from cylinder 130 to reaction chamber 150. While valve 132 typically is positioned on the output of cylinder 130, the valve may be positioned anywhere between cylinder 130 and the input of reaction chamber 150, and cylinder 130 may simply include an on/off valve.

Figure 2:
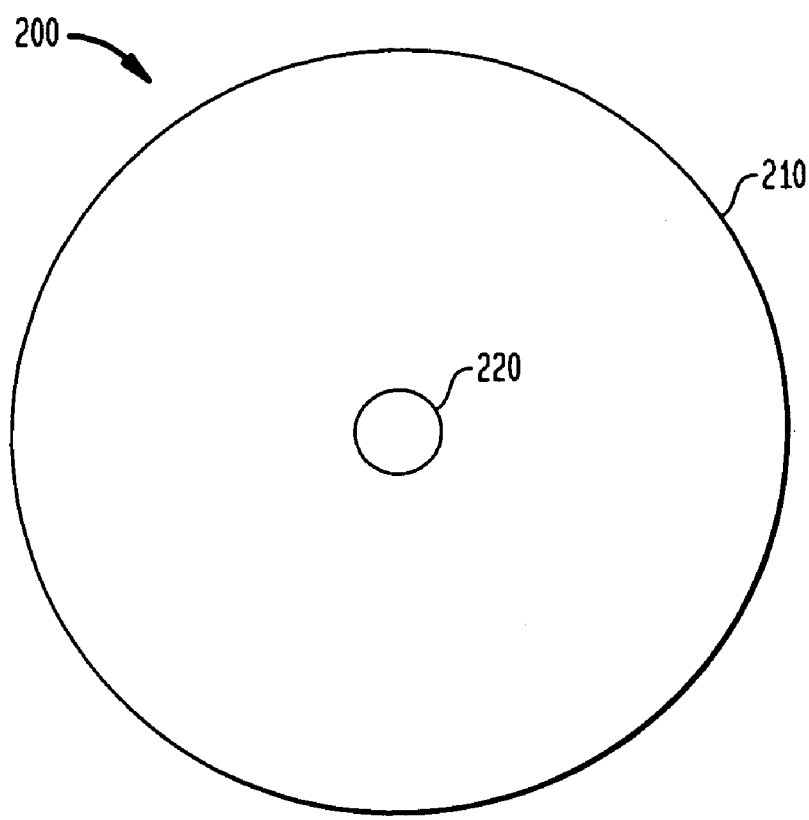
FIG. 2 is a front elevational view of an orifice plate for use in the system for creating a mercury halide standard of FIG. 1.

The reaction chamber 150 preferably has a first controller 151 for controlling and measuring the flow of the gaseous elemental mercury into reaction chamber 150, and a second controller 152 for controlling and measuring the flow of the chlorine gas into reaction chamber 150. Conduit 120 from cylinder 110 is input to controller 151, and conduit 140 from cylinder 130 is input to controller 152. In a preferred embodiment, controller 152 is an orifice plate 200. As shown in FIG. 2, orifice plate 200 is a generally flat plate 210 having an orifice or aperture 220 of a predetermined size. By selecting an aperture 220 having an appropriate size, a desired rate of flow between conduit 140 and reaction chamber 150 can be achieved.

Since the concentration of the halogen donor in the halogen donor source is known, as is the flow rate of the halogen donor, the amount of halogen donor flowing into reaction chamber 150 can be controlled. Preferably, the flow of the halogen donor is controlled so that the amount of the halogen donor supplied to reaction chamber 150 is the same as or greater than the amount of mercury supplied to reaction chamber 150. The amount of the halogen donor preferably should be between at least a stoichiometric amount based upon the amount of mercury supplied to reaction chamber 150 and about one hundred times the amount of mercury supplied to reaction chamber 150, and more preferably between about two and about five times the amount of mercury supplied to reaction chamber 150. Such amounts of halogen donor will assure that substantially all of the gaseous elemental mercury supplied to reaction chamber 150 will be reacted to the halide form.

A conduit 153 leads from controller 151, and a conduit 154 leads from controller 152. Conduits 153 and 154 connect to one another at a junction 155. Junction 155 may include multiple inputs that join together so that the contents passing through the inputs come together at the junction. In addition to conduit 153 supplying gaseous elemental mercury and conduit 154 supplying a halogen donor, other inputs to junction 155 may supply other halogen donors or nitrogen gas, for use in testing the mercury analyzer system's ability to read zero mercury content, or flushing the reaction chamber of gases. Junction 155 may have any configuration including, for example, a T-shape or Y-shape, as shown in FIG. 1. A conduit 156 leads from junction 155 to the output 158 of reaction chamber 150. As will be explained below, the gaseous elemental mercury and the halogen gas combine in reaction chamber 150 to form mercury halide gas which flows out from reaction chamber 150 through the output 158. In order to speed this reaction, the contents of conduit 156 may be heated. While any suitable arrangement may be used to perform this heating function, in a preferred arrangement, conduit 156 is coiled around an electric or other heating element 157 which heats the contents of the conduit to a temperature in a range between about 30° C. and about 700° C., and more preferably, between about 250° C. and about 500° C. It is known that heating gaseous elemental mercury and chlorine gas causes the reaction to form mercury chloride to occur more rapidly. As a result, the elemental mercury may be fully converted to mercury chloride in a shorter length of conduit 156. Of course, it will be appreciated to one skilled in the art that reaction chamber 150 need not be heated. In such event, however, the reaction occurs at a much slower rate, and reaction chamber 150 may need to be longer to allow the gases more time to react.

A conduit 160 attached to the output 158 of reaction chamber 150 directs the mercury halide gas to an input 172 of mercury analyzer system 170. The typical mercury analyzer system has multiple parts, as can be seen in the aforementioned U.S. Pat. No. 6,475,802, the disclosure of which is hereby incorporated by reference herein. Thus, system 170 includes an analyzer 175 for measuring mercury content. Analyzer 175 ordinarily can make readings only of elemental mercury, $Hg^0$. Accordingly, system 170 typically also includes at least one module 174 for converting non-elemental mercury to elemental mercury so that it may be read by analyzer 175. This enables the analyzer 175 to make a complete measurement of the mercury content in a specimen. The present invention can be used to ensure that module 174 is properly converting mercury halide into elemental mercury, and thus that the mercury in the mercury halide is being measured by analyzer 175.

Mercury analyzer systems are structured in many different ways. For example, there may be more than one module for converting mercury halide to elemental mercury. Also, module 174 for converting mercury halide into elemental mercury may be in the form of a separate device positioned apart from, and prior to, analyzer 175. Mercury analyzer systems, alternatively, may have separate modules for converting different forms of non-elemental mercury to elemental mercury. Hence, the present invention is not limited to mercury analyzer systems having only one such conversion module or to analyzer systems having conversion modules which are integrated with the mercury analyzer.

The operation of system 100 to create a mercury halide standard and the use of that standard to test the operation of analyzer 175 will now be described. Initially, the valve 112 on cylinder 110 is opened such that the pressure inside cylinder 110 forces the gaseous elemental mercury to flow through conduit 120 to controller 151. The flow of the gaseous elemental mercury is regulated by controller 151 so that the gas flows into conduit 153 and towards junction 155 at a known flow rate. Similarly, valve 132 on cylinder 130 is opened whereby the pressure inside cylinder 130 forces the chlorine gas to flow through conduit 140 to pressure and flow controller 152. The flow of the chlorine gas is regulated by controller 152 so that the gas flows into conduit 154 and towards junction 155 at a known flow rate. Since the concentrations and flow rates of the gases are known, the amount of gaseous elemental mercury and the amount of chlorine gas entering junction 155 can be determined. At junction 155 the gases begin to mix and react to form mercury chloride, $HgCl_2$. For every mole of elemental mercury, $Hg^0$, reacted, one mole of chlorine, $Cl_2$, is needed to form mercury chloride, $HgCl_2$. Therefore, the amount of chlorine in reaction chamber 150 should be at least a stoichiometric amount, and preferably in excess of the amount of mercury to ensure that all the gaseous elemental mercury is converted into mercury chloride. This excess may be provided by using the same gas flow rates, but a concentration of the chlorine gas which is higher than that of the gaseous elementary mercury, or by using a higher flow rate of chlorine gas as compared to the flow rate of the gaseous elemental mercury when their concentrations are similar. This allows the amount of mercury chloride to be the same as the amount of the gaseous elemental mercury supplied from the gas cylinder. Other halogen donors may not react in the same one-to-one ratio with elemental mercury as does chlorine, so other halogen donors may need to be provided at higher or lower concentrations or at higher or lower flow rates to compensate for the difference in this reaction ratio.

The reaction proceeds as the gases travel along conduit 156 and are heated by heater 157. The mercury halide forms and flows to the output 158 of reaction chamber 150, and from there via conduit 160 to the input 172 of mercury analyzer system 170. Within analyzer system 170, the mercury halide is first converted in module 174 to elemental mercury, such that gaseous elemental mercury is reformed. From module 174 the reformed gaseous elemental mercury, as well as any unconverted mercury halide gas and any unreacted remnant gas, are fed to analyzer 175 where a measurement is made of the amount of mercury in the sample. The measurement can then be compared to the known amount of mercury halide, which is equal to the amount of gaseous elemental mercury initially supplied to reaction chamber 150, i.e., the amount of mercury supplied by gas cylinder 110. This comparison can be made either manually by simply comparing the subject values, or automatically by devices well known to those skilled in the art, such as data analysis software and the like. The result of the comparison can be used to determine the degree by which the mercury analyzer system 170 converts mercury chloride to elemental mercury.

In an alternative method, since the amount of gaseous elemental mercury supplied to reaction chamber 150 is known, and since it is assumed that all of that gaseous elemental mercury is converted to mercury halide, the measurement of the amount of reformed gaseous elementary can be compared directly with the known amount of gaseous elemental mercury supplied to the reaction chamber to determine a degree of conversion. Thus, if any of the mercury halide is not converted back to gaseous elemental mercury by conversion module 174, the amount of mercury measured by analyzer 175 will be less than the known amount of gaseous elemental mercury supplied to reaction chamber 150.

Figure 3:
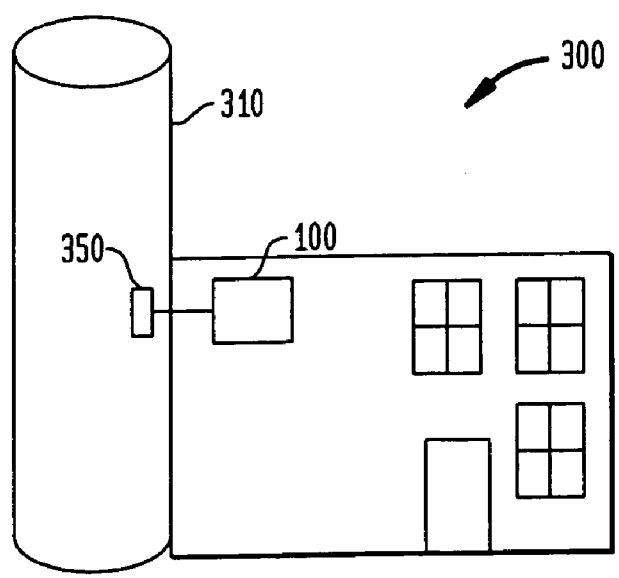
FIG. 3 is a highly schematic diagram showing the use of the system of the present invention in an industrial facility.

Mercury analyzer systems, such as system 170, are often used in industrial facilities that are exposed to mercury, including fossil fuel burning plants, incinerators, chemical producing plants, and other facilities that use mercury or that have mercury as a reactant, product, byproduct, or catalyst, or that otherwise have a need or desire to measure mercury. For example, fossil fuel burning plants measure the amount of mercury present in the byproducts of a combustion reaction. These byproducts frequently include mercury in halide form. One such industrial facility 300 is shown schematically in FIG. 3. In such facilities 300, the reaction byproducts are vented to the atmosphere through a smoke stack 310. Typically, somewhere along smoke stack 310 is an area 350 that allows a sample of the stack gas to be drawn off. The drawn off gas is diverted to a mercury analyzer system to measure the amount of mercury in the reaction byproducts being vented. The present invention may be used in this environment to test the mercury analyzer system's ability to accurately measure the amount of mercury in the stack gas.

The invention can also be used such that a portion of the gaseous elemental mercury is left unreacted with the halogen donor. This can be done by having a lower concentration of halogen donor than gaseous elemental mercury at similar flow rates, or by having a much lower flow rate of the halogen donor than gaseous elemental mercury at similar concentrations. The mercury analyzer 175 should still read the total amount of gaseous elemental mercury added to the reaction chamber because it will measure both the unreacted elemental mercury and the elemental mercury reacted to form mercury halide and then converted by module 174 back into elemental mercury. Unless the portion that is unreacted is known, however, it will be unknown what part of the mercury analyzer system is not properly working if the mercury analyzer does not read the total amount of mercury added to the reaction chamber.

Optionally, one can use the present invention to test a mercury analyzer system's ability to read elemental mercury. Gaseous elemental mercury having a known concentration can be passed through conduit 120 and into reaction chamber 150, while no halogen donor is supplied to reaction chamber 150. The gaseous elemental mercury then passes through the reaction chamber and into the mercury analyzer system unchanged. The mercury analyzer then directly measures the amount of elemental mercury. This test can be used to calibrate the analyzer's ability to detect elemental mercury.

Another optional test can be performed to test the ability of the reaction in the reaction chamber to form mercury halide. After the gaseous elemental mercury has reacted with the halogen donor to form mercury halide, the reaction products may be supplied to the mercury analyzer system such that they bypass module 174 and therefore are not converted into elemental mercury. Since mercury analyzer 175 only measures elemental mercury, if all of the elemental mercury has been converted into mercury halide in reaction chamber 150, the mercury analyzer should measure no elemental mercury in the reaction products. Therefore, any measurement of elemental mercury would represent an incomplete conversion to the halide form.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as set forth in the appended claims.

The invention claimed is:

1. A method of creating a mercury halide standard to test a mercury analyzer system, comprising:
   providing an amount of gaseous elemental mercury of a known concentration, said gaseous elemental mercury being provided from a gas cylinder;
   providing at least a stoichiometric amount of at least one halogen donor which is reactable with said amount of known concentration of gaseous elemental mercury;
   reacting said amount of known concentration of gaseous elemental mercury with said stoichiometric amount of said halogen donor to form an amount of a gaseous mercury halide standard of known concentration;
   supplying said mercury halide standard of known concentration to a mercury analyzer system;
   performing a conversion from said gaseous mercury halide standard to elemental mercury within said mercury analyzer; and
   testing the completeness of the conversion.

2. The method as claimed in claim 1, wherein said halogen donor donates chlorine.

3. The method as claimed in claim 1, wherein said halogen donor is a gas.

4. The method as claimed in claim 3, wherein said gas is chlorine gas.

5. The method as claimed in claim 1, wherein said halogen donor is provided from a gas cylinder.

6. The method as claimed in claim 1, wherein said mercury halide is mercury chloride.

7. A method of creating a mercury halide standard, comprising:
   providing an amount of gaseous elemental mercury of a known concentration;
   providing at least a stoichiometric amount of at least one halogen donor which is reactable with said amount of known concentration of gaseous elemental mercury;
   reacting said amount of known concentration of gaseous elemental mercury with said stoichiometric amount of said halogen donor to form an amount of a gaseous mercury halide standard of known concentration;
   supplying said mercury halide standard of known concentration to a mercury analyzer system;
   performing a conversion from said gaseous mercury halide standard to elemental mercury within said mercury analyzer; and
   testing the completeness of the conversion.

* * * * *